United States Patent
Comaniciu et al.

(10) Patent No.: US 7,087,018 B2
(45) Date of Patent: Aug. 8, 2006

(54) SYSTEM AND METHOD FOR REAL-TIME FEATURE SENSITIVITY ANALYSIS BASED ON CONTEXTUAL INFORMATION

(75) Inventors: Dorin Comaniciu, Princeton, NJ (US); Arun Krishnan, Exton, PA (US); Xiang Sean Zhou, Plainsboro, NJ (US); Bhavani Duggirala, Bellevue, WA (US); Diane Paine, Redmond, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 83 days.

(21) Appl. No.: 10/702,984

(22) Filed: Nov. 6, 2003

(65) Prior Publication Data
US 2004/0133083 A1   Jul. 8, 2004

Related U.S. Application Data

(60) Provisional application No. 60/425,820, filed on Nov. 13, 2002, provisional application No. 60/425,800, filed on Nov. 13, 2002.

(51) Int. Cl.
*A61B 5/00* (2006.01)
*A61B 8/00* (2006.01)

(52) U.S. Cl. .................. 600/300; 600/437
(58) Field of Classification Search ........ 600/300–301, 600/407, 409, 425, 427, 437, 443, 447, 473, 600/476, 481, 483, 485, 500, 504, 509, 513, 600/529, 544, 549
See application file for complete search history.

(56) References Cited

U.S. PATENT DOCUMENTS

| | | | | |
|---|---|---|---|---|
| 5,235,510 | A | | 8/1993 | Yamada et al. ......... 364/413.02 |
| 5,596,993 | A | * | 1/1997 | Oriol et al. ................. 600/511 |
| 5,769,074 | A | * | 6/1998 | Barnhill et al. ............. 600/300 |
| 5,776,063 | A | * | 7/1998 | Dittrich et al. ............. 600/408 |
| 5,799,100 | A | | 8/1998 | Clarke et al. ............... 382/132 |
| 5,839,438 | A | * | 11/1998 | Graettinger et al. ......... 600/300 |
| 5,999,639 | A | * | 12/1999 | Rogers et al. .............. 382/132 |
| 6,032,678 | A | | 3/2000 | Rottem ....................... 128/920 |
| 6,090,044 | A | * | 7/2000 | Bishop et al. .............. 600/300 |
| 6,246,782 | B1 | * | 6/2001 | Shapiro et al. ............. 382/128 |
| 6,320,976 | B1 | | 11/2001 | Murthy et al. .............. 382/128 |

OTHER PUBLICATIONS

"Efficient Interpretation Policies", Isukapalli et al., in Proc. IJCAI, 2001.
"Filters, Wrappers and a Boosting-Based Hybrid for Feature Selection", S. Das, in Proc. ICML, 2001.
"Vision for Mobile Robot Navigation: A Survey", DeSouza et al., IEEE Transactions on Pattern Analysis and Machine Intelligence, vol. 24, No. 2, Feb. 2002, pp. 237-267.

(Continued)

*Primary Examiner*—Francis J. Jaworski
(74) *Attorney, Agent, or Firm*—Michele L. Conover

(57) ABSTRACT

A system and method for assigning feature sensitivity values to a set of potential measurements to be taken during a medical procedure of a patient in order to provide a medical diagnosis is disclosed. Data is received from a sensor that represents a particular medical measurement. The received data and context data are analyzed with respect to one or more sets of training models. Feature sensitivity values are derived for the particular medical measurement and other potential measurements to be taken based the analysis, and the feature sensitivity values are outputted.

36 Claims, 3 Drawing Sheets

OTHER PUBLICATIONS

"Some Slutions to the Missing Feature Problem in Vision", Ahmad et al., Advances in Neural Information Processing Systems 5, Morgan Kaufmann Publishers, San Mateo, CA.

"Autonomous Exploration Using Multiple Source of Information", Moorehead et al., Proceedings of the 2001 IEEE Int'l Conference on Robotics & Automation, Seoul, Korea, May 21-26, 2001, pp. 3098-3103.

"A Mathematical Programming Approach to the Kernel Fisher Algorithm", Mika et al., in NIPS 13, 2001.

"Using Mutual Information for Selecting Features in Supervised Neural Net Learning", R. Battiti, IEEE Transactions on Neural Networks, vol. 5, No. 4, Jul. 1994, pp. 537-550.

"Learning from Incomplete Data", Ghahramani et al., in NIPS6, 1994.

"Active Sensing for Robotics—A Survey", Mihaylova et al, in Proc. 5th Int'l Conf. on Numerical Methods and Applications, 2002.

"Learning Active Vision", Kappen et al., in Proc. ICANN, Oct. 1995.

"Active Vision for Complete Scene Reconstruction and Exploration", Marchand et al., IEEE Transactions on Pattern Analysis and Machine Intelligence, vol. 21, No.1, Jan. 1999, pp. 65-72.

"Transinformation for Active Object Recognition", Schiele et al., ICCV, 1998.

"Information Theoretic Sensor Data Selection for Active Object Recognition and State Estimation", Denzler et al., IEEE Trans. On Pattern Analysis and Machine Intelligence, vol. 24, No. 2, Feb. 2002, pp. 145-267.

"Feature Space Trajectory Methods for Active Computer Vision", Sipe et al., IEEE Trans. On Pattern Analysis and Machine Intelligence, vol. 24, No. 12, Dec. 2002, pp. 1634-1643.

"Viewpoint Selection by Navigation through Entropy Maps", Arbel et al., ICCV, Corfu, Greece, Sep. 1999.

"Training Neural Networks with Deficient Data", Tresp et al., Advances in Neural Information Processing Systems 6, San Mateo, CA, Morgan Kaurman, 1994.

"Medical Image Databases: A Content-based Retrieval Approach", American Medical Informatics Association, http://www.pubmedcentral.nih.gov/articlerender.fcgi?artid=61234.

"Classification Driven Semantic Based Medical Image Indexing and Retrieval", Liu et al., 1998 Carnegie Mellon University.

"Fast and Effective Retrievel of Medical Tumor Shapes", Korn et al., IEEE Transactions on Knowledge and Data Engineering, vol. 10, No. 6, Nov./Dec. 1998, pp. 889-904.

"Joint Induction of Shape Features and Tree Classifiers", German et al., May 1996.

"Image-guided decision support system for pathology", Comaniciu et al., Machine Vision and Applications (1999), pp. 213-224.

"Content-Based Retrieval from Medical Imaging Databases: A Synergy of Human Interaction, Machine Learning and Computer Vision", Brodley et al., 1999, American Assoc. for Artificial Intelligence.

"Toward Validation Databases for Medical Imaging: Engineering a Scientific Rendezvous", Yoo, National Library of Medicine, National Institutes of Health, Bethesda, MD.

"Content-Based Image Retrieval in Medical Applications: A Novel Multi-Step Approach", Lehmann et al., Part of the IS&T/SPIE Conf. on Storage and Retrieval for Media Databases 2000, San Jose, CA, Jan. 2000, SPIE vol. 3972, pp. 321-320.

U.S. Appl. No. 10/654,509, filed Sep. 3, 2003 entitled "Remote Assistance for Medical Diagnostic Ultrasound".

* cited by examiner

SYSTEM AND METHOD FOR REAL-TIME FEATURE SENSITIVITY ANALYSIS BASED ON CONTEXTUAL INFORMATION

CROSS REFERENCE TO RELATED APPLICATIONS

This application claims the benefit of U.S. Provisional Application Ser. No. 60/425,800 and 60/425,820 filed on Nov. 13, 2002, which is incorporated by reference herein in its entirety.

TECHNICAL FIELD

The present invention is directed to a system and method for real-time feature sensitivity analysis based on contextual information, and more particularly, to a system and method for real-time feature selection of measurements to be taken during a medical testing procedure based in part on contextual information in order to accurately diagnose a medical condition.

BACKGROUND OF THE INVENTION

Active object recognition or active vision (or as called in robotics, active sensing/localization/navigation) deals with a specific object or scene, searching for the next action, operator, or viewpoint, to optimize some objective function. Although these topics are intimately related to feature selection in machine learning, two key issues raised in the latter field have not been consciously considered by the former, namely, the necessity of an induction algorithm, and the possibility of complex feature interactions (e.g., in-class dependencies).

As a result, an active vision system based on ad hoc heuristics may fail to fully reveal potential feature contributions. For example, most existing systems implicitly assume feature independence (which translates to viewpoint independence for object recognition using an active camera). However, in many cases two or more views are required to discriminate one class of objects from others.

Much research in active vision and robotics has used similar heuristics for active selection of best features. Some techniques include using reduction of entropy to guide the selection of viewpoints, optimal sensor parameter selection for iterative state estimation in static systems by maximizing mutual information, and information gain-based selection of "imaging operators", taking into account also operation costs. However, none of the above techniques formally addresses the role of an induction algorithm for feature analysis as well as the issue of feature interaction.

Feature selection for classification has recently also been very active. Feature selection is essentially a search for the most sensitive feature subset for the purpose of improved classification accuracy and a significantly reduced feature set. However, existing feature selection paradigm does not deal with a specific test input or case-in-question along with a context. Furthermore, many known feature selection techniques do not use an induction algorithm for feature analysis or address the issue of feature interaction.

One traditional class of feature selection techniques uses a filter model that treats feature selection solely as a pre-processing step for later induction algorithm design. Recent feature selection techniques use a wrapper model that performs cross validation using an induction algorithm on the training set. There have also been efforts to link these two models. However, these algorithms are not directly applicable for conditional feature sensitivity analysis.

For example, the wrapper approach relies on cross validation but oftentimes sufficient training samples do not exist to cross-validate in the neighborhood defined by the context—especially when more than a few features have been measured; on the other hand, most variants of the filter approach do not address the context issue, and often ignore the induction algorithm altogether. Consulting an induction algorithm is necessary during the course of feature evaluation, because the most sensitive feature is not necessarily the one that leads to the most variability in labels (which may lead to minimal empirical error on the training data but large error on test data); the best feature shall lead to the most systematic and predictable variability in labels. The present invention combines the essence of both the wrapper model and the filter model and puts an explicit emphasis on the modeling of contextual features.

For example during an echocardiograph exam, the number of possible measurements is in the hundreds, but a typical echocardiograph exam in the United States only contains about ten different measurements on average. The appropriate selection of additional measurements requires extensive training and field experience and is therefore subjective and error-prone. It would be very helpful if a machine could provide context-sensitive real-time guidance as to what additional feature(s) should be measured for the current case. A feature sensitivity analysis module also provides a way to reduce medical costs by identifying a minimal number of measurements that need to be performed to provide a proper medical diagnosis.

SUMMARY OF THE INVENTION

The present invention is directed to a method for assigning feature sensitivity values to a set of potential measurements to be taken during a medical procedure of a patient in order to provide a medical diagnosis. Data is received from a sensor that represents a particular medical measurement. The received data and context data are analyzed with respect to one or more sets of training models. Feature sensitivity values are derived for the particular medical measurement and other potential measurements to be taken based the analysis, and the feature sensitivity values are outputted.

The present invention is also directed to a system for assigning feature sensitivity values to a set of potential measurements to be taken during a medical procedure of a patient in order to provide a medical diagnosis. A medical sensor provides data pertaining to medical measurements taken of a patient. A processor connected to the medical sensor receives the data from the medical sensor and context data relating to the patient. The processor analyzes the sensor data and context data and determines feature sensitivity values for a set of potential measurements to be taken by the sensor. A display device displays the sensor data and feature sensitivity values.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a method for assigning feature sensitivity values to a set of potential measurements to be taken during a medical procedure in order to select those measurements having the highest feature sensitivity thereby achieving a proper medical diagnosis with a minimal number of measurements being taken. Feature selection is essentially a search for the most sensitive feature subset for the purpose of improved classification accuracy and a significantly reduced feature set. The present invention addresses feature selection that further includes a specific test input or case-in-question along with a context. For any given medical diagnosis, all features for a given case are presumed to be uncertain but to different degrees—a measured feature (e.g., the visible patterns from the current camera angle) contains lower uncertainty, while a missing feature (e.g., the unseen or self-occluded parts of an object) has maximal uncertainty. Then, the question is: "given an induction algorithm, a labeling on a training set, and some contextual information for the case-in-question, what is the relative sensitivity for all features?" In other words, if more measurements are taken, either on unmeasured features, or to increase the accuracy of measured features, what additional measurements should be taken? The present invention is directed to how to evaluate the importance or sensitivity of the features or measurements, as well as how to deal with uncertainty in the contextual features, which will be described in more detail hereinafter.

Figure 1:
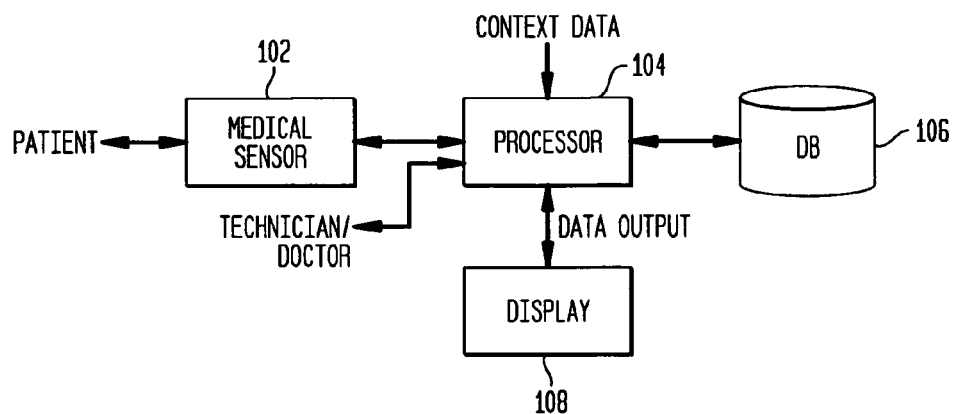
FIG. 1 is a block diagram of a system for implementing a method for conditional feature sensitivity analysis in accordance with the present invention.

FIG. 1 illustrates an exemplary architecture of an echocardiograph system that uses a method for identifying conditional feature sensitivity in accordance with the present invention. A medical sensor 102, such as an ultrasound transducer is used to perform an examination on a patient. The sensor 102 is used to obtain medical measurements consistent with a particular medical examination. For example, a patient experiencing heart problems may have an echocardiogram performed to help diagnose the particular heart ailment. In such an instance, the medical sensor 102 may be an ultrasound transducer. An ultrasound system provides two- or three-dimensional images of the heart from various perspectives.

The present invention will be described in detail in the context of performing an echocardiogram examination. However, it is to be understood by those skilled in the art that the present invention can be used in conjunction with other medical examinations such as, but not limited to, breast cancer detection examinations, prenatal ultrasound examinations or another type of medical examination in which a diagnosis is being determined.

The information obtained by the sensor 102 is communicated to a processor 104 which may be a workstation or personal computer. The processor 104 converts the sensor data into an image that is communicated to display 108. The display 108 may also communicate other graphical information or tables of information relating to the image. In accordance with the present invention, the processor 104 is also provided with context data which is used in conjunction with the sensor data to determine what, if any, further measurements need to be taken by the sensor 102 in order to provide a proper medical diagnosis.

As will be described in greater detail hereinafter, context data can originate from a number of sources of information including, but not limited to, vital statistics, patient symptoms and available test data. Vital statistics can include such information as a patient's height, weight, age, blood pressure measurement, or any other personal medical data that is pertinent to the particular medical examination being performed. Patient symptoms can include, for example, indications of pain, such as chest pain, shortness of breath, detection of a foreign mass in an area of tissue, labored breathing, poor circulation, unexplained weight loss or gain or any other symptom that would be material to a particular medical examination. Available testing data can come from a baseline scan, preliminary blood work or any other test that would be material to a particular medical examination, and the data from sensor 102 during the current examination. Testing data can also include test results or medical measurements taken from a patient's prior medical examinations or procedures. Furthermore, context data may also include data pertaining to the ultrasound or other medical diagnosis system. For example, context data may include the type of exam being taken, various system settings and view settings.

Upon receipt of the data from the medical sensor 102, the processor 104 retrieves training models from a database 106 in order to perform feature sensitivity analysis as will be described in greater detail hereinafter. In addition to data from the medical sensor, the processor 104 may also receive other data inputs. For example, the processor may receive data from the technician or physician performing the medical procedure. The processor 104 may also receive other measurements or system data to be considered during the feature sensitivity analysis. The training models contain a collection of data measurements relating to one or more particular medical conditions. For example, the database may contain a plurality of distribution data points relating to the likelihood of a patient having Dilated Cardiomyopathy (DCM) or a normal heart condition (nonDCM). Such data may include measurements pertaining to the size of the heart, the thickness of the heart walls and the level of blood flow to and from the heart.

Figure 3:
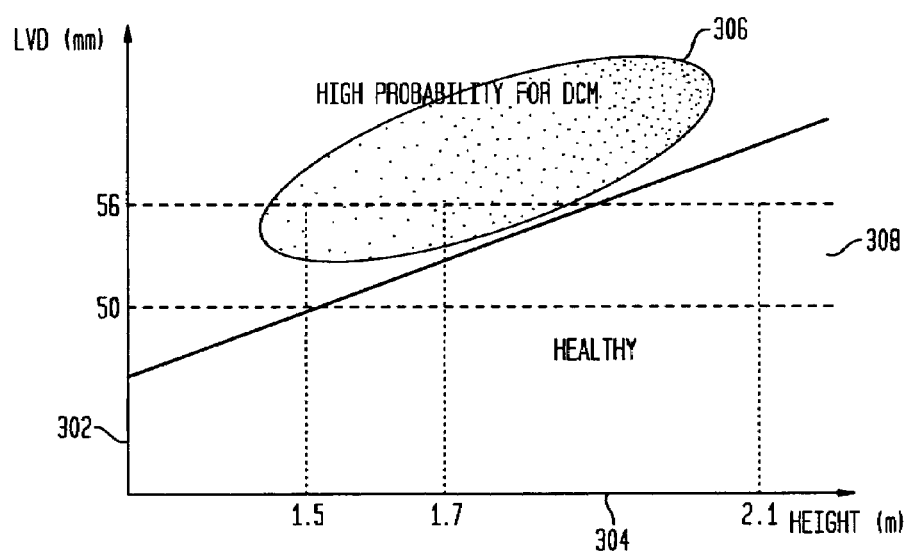
FIG. 3 is a graph depicting the training models used to determine if a patient has DCM.

FIG. 3 illustrates a graph that represents a distribution of training models indicating the probability of DCM. The vertical axis 302 represents Left Ventricle Dimensions (LVD) in millimeters (mm) and the horizontal axis 304 represents the patient's height in meters (m). A training model distribution 306 indicates those measurements that signify a high probability of DCM and a second training model distribution 308 indicates those measurements that signify a high probability of nonDCM.

Consistent with FIG. 3, for a patient with a height of 1.5 m to 1.7 m and an LVD of 5056 mm, the patient should definitely be re-measured more precisely for a sure diagnosis. This is because the patient has a somewhat high probability of having DCM. However, the same LVD value range is adequate and should not be a sensitive concern at all for a person taller than 2 m. Also, the LVD measurement will not be a sensitive measurement for a 1.1 m child because then it is almost certain a DCM case.

Other information may be included in the database 106 as well including image data that represents a particular medical condition (e.g., images of hearts that have various types of DCM) as well as other groupings of data that may be useful in achieving a correct medical diagnosis.

Figure 2:
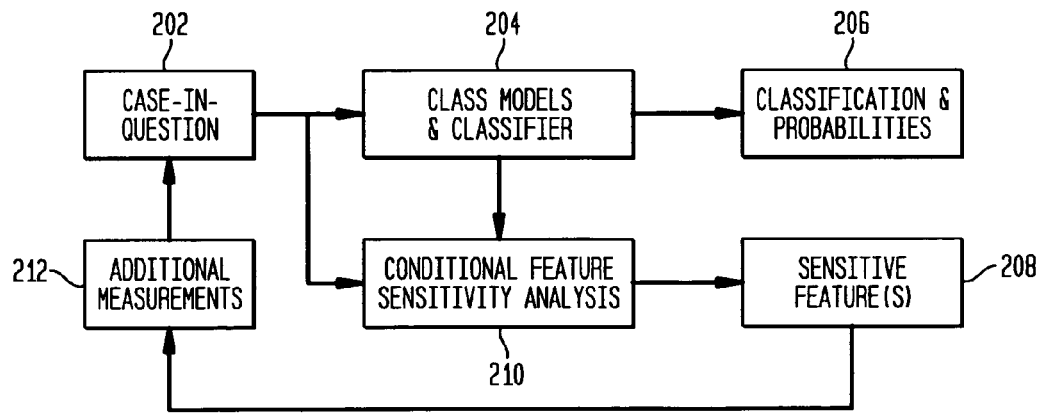
FIG. 2 is a functional block diagram illustrating the overall process for conditional feature sensitivity analysis.

FIG. 2 illustrates a flow diagram that illustrates the real-time guidance of the measurement process during a particular medical examination. The conditional feature sensitivity analysis module 210 takes as inputs all the available information about the case in question 202 (both missing and uncertain features) together with the class models 204 (e.g., likelihood maps) provided by a given induction algorithm. The output is a list of sensitive features 208 that provides a list of additional measurements 212 that should be measured next, to maximally reduce uncertainty in classification.

Figure 4:
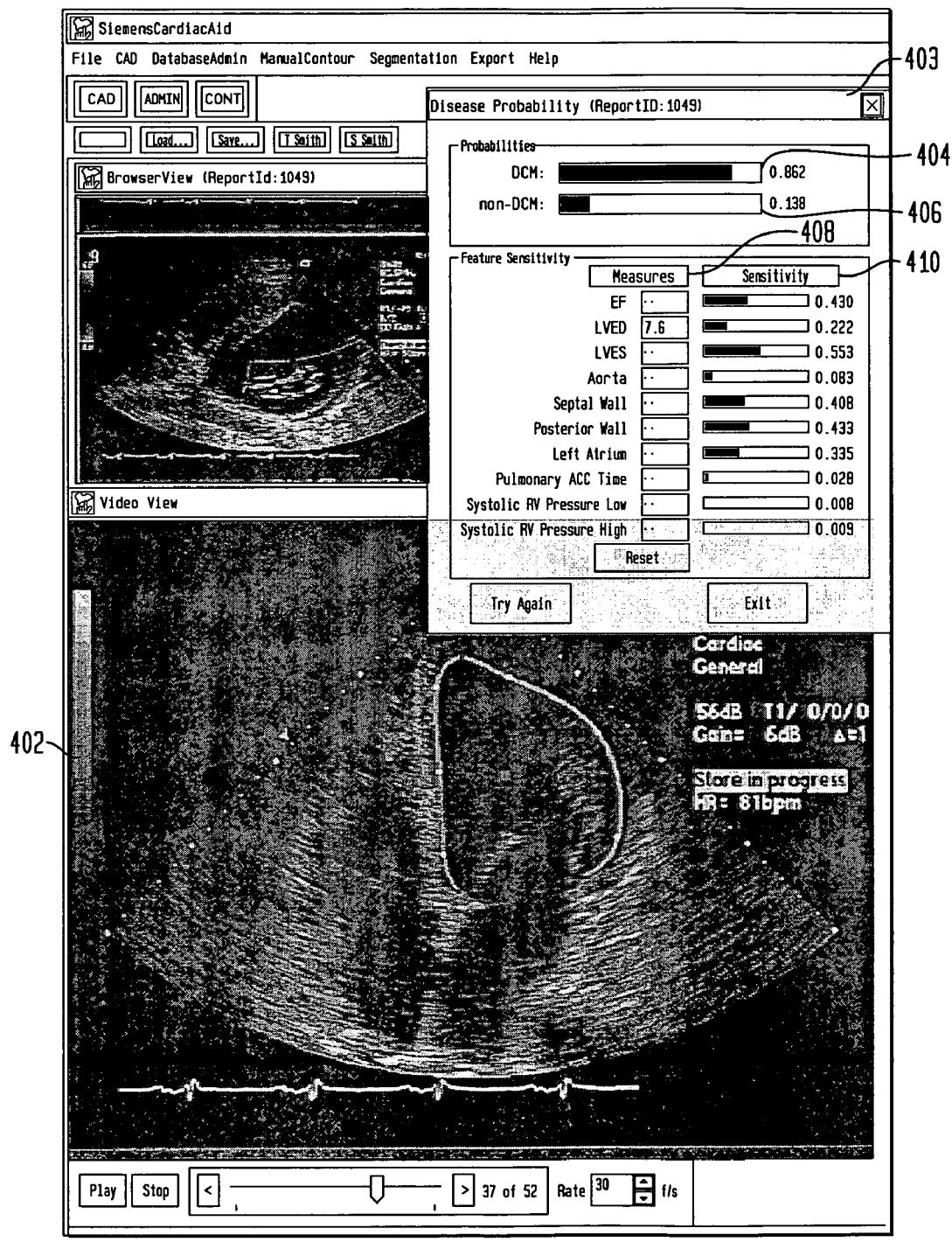
FIG. 4 is an exemplary display screen showing image and feature sensitivity data in accordance with the present invention.

Referring back to FIG. 1, once a particular measurement has been taken and the feature sensitivity analysis performed, the output is provided on display 108. An exemplary display screen is shown in FIG. 4. The screen includes an ultrasound image 402 created based on data received from the medical sensor 102 which displays views of the heart from which Left Ventricle End Diastolic (LVED) dimension measurements can be made. LVED provides an indication of the size of the heart. Also included in the screen is a graphic 403 that provides the probability of DCM vs. nonDCM as well as an indication of measurements 408 that have been taken or can be taken and the corresponding sensitivity value 410 for each measurement.

In accordance with the present invention, the sensitivity value provides an indication of the importance of a particular measurement for determining a correct medical diagnosis. For example, as illustrated in FIG. 4, the LVED measurement is 7.6 which indicates a high probability of DCM. The sensitivity values indicate that other measurements are recommended being taken that include the Left Ventricle End Systolic (LVES) dimension, as well as the wall thickness (septal wall, posterior wall) and the Ejection Fraction (EF).

A technician or doctor who is viewing this screen can then determine, depending upon the known facts regarding the patient, whether these additional measurements need to be taken. If any of these subsequent measurements are made, the graphic 403 is updated both with the DCM/nonDCM probability as well as re-calculate the feature sensitivities for the measurements. By performing these feature sensitivity analyses, the technician or doctor is able to achieve a correct medical diagnosis by performing both the "best" measurements and the fewest number of measurements.

An exemplary system for real-time diagnosis support in echocardiography with optical flow-based contour tracking for calculating heart volume, ejection fraction, and ischemia regions, etc. will now be described in conjunction with FIG. 4. The exemplary system uses a database with about 2000 echocardiography videos, labeled by medical expert into different types and stages of cardiomyopathies. As discussed above, FIG. 4 shows the system at work for diagnosing DCM or nonDCM: after LVED (left ventricle end diastolic dimension) is measured to 7.6 cm (95% th percentile of healthy heart is <5.8 cm), the system outputs a probability of DCM at 86.2%, but recommended further measurements on LVES (LV end systolic dimension), wall thickness, EF (ejection fraction), etc., in that order.

If the doctor or technician decide to do a further measurement (e.g., LVES), the feature sensitivity analysis is recalculated and new sensitivity values are determined as well as new probability values of DCM vs. nonDCM based on the additional measurement. For each additional measurement that may be performed, the outputs are again recalculated. Based on the resulting probability results, the doctor or technician can determine if further measurements are required or if a proper medical diagnosis has been achieved.

For DCM vs. nonDCM, LVED is the most sensitive feature given no context. Subsequent feature sensitive ordering is case or context-dependent, assuming nonlinear class boundaries. In an embodiment of the present invention, once the doctor or technician has completed those measurements which he or she believes are necessary to achieve a proper medical diagnosis, the data may be added to the data base to further update the training models.

The present invention is directed to how to deal with uncertainty with respect to the contextual features. Consistent with the above, from an algorithm viewpoint, a feature with uncertainty models both a missing feature and a measured feature. In other words, all features will be treated as uncertain features, with different degrees of uncertainty. As such, a case S has a measurement vector Z with M features, each of which has a prior distribution $p_0(z)$ over the whole population, a true value z for the current case, and a posterior distribution $p(z)$ after a measurement operation. The ultimate goal is probabilistic classification, i.e., given a case $S_i$, to obtain probabilities of its membership in all classes: $\{P(C_i=c_1), P(C_i=c_2), \ldots, P(C_i=c_K)\}$, where $c_k$, $k=1, 2, \ldots, K$, are the class labels.

The symbol y represents the feature under current study, $\{y\} \subseteq Z$. Without loss of generality we will assume y is 1–D for simplicity unless otherwise noted. The remaining features are represented by a vector X, $X=Z\backslash\{y\}$. The current features are referred to as y, and the contextual features as X. Context—i.e., what we know about the current case—is denoted by $\chi$ and $\zeta$, representing the distributions of X and y, respectively. The expression "$y \in \zeta$" means "y has a distribution $\zeta$" or "y is restricted to $\zeta$." A particular sample drawn from $\zeta$ is denoted by $y_i$; and from X, $x_j$. Note that when y is in 1–D, $x_j$ is a (N–1)-dimensional vector. The lowercase x (without a subscript) is used to represent a subset of Z.

A prerequisite for what is described hereinafter is a way to deal with missing or uncertain features for both training and testing. A principled way of treating a missing feature is to sample (for training) or integrate (for testing) over its value range (or, its conditional distribution), an idea that parallels the EM and Bayesian treatments of missing data. A traditional formulation is as follows:

$$P(C = c_k \mid X \in \chi, y \in \zeta) = \frac{\int_\chi \int_\zeta P(X, y) P(C = c_k \mid X, y) dX dy}{P(X \in \chi, y \in \zeta)} \quad (1)$$

P(C|X, y) is obtained from the classifier. An estimation of the joint distribution of the features, P(x, y) is also required. It is assumed that a likelihood function is available for every class in the original feature space P(X, y|C) (these can be approximated efficiently), joint distribution is implied and the following formula is used:

$$P(C = c_k \mid X \in \chi, y \in \zeta) = \frac{P(C = c_k) \int_\chi \int_\zeta P(X, y \mid C = c_k) dX dy}{\sum_k P(C = c_k) \int_\chi \int_\zeta P(X, y \mid C = c_k) dX dy} \quad (2)$$

Here $P(C=c_k)$ is the prior probability of the kth class.

The concept of conditional feature sensitivity is defined as follows: Given the context $\{\epsilon\chi, y\epsilon\zeta\}$ for the case in question, further measurement of which feature(s) can maximally reduce uncertainty in classification? Although other criteria exist, the best gauge for uncertainty is entropy. The reduction of entropy is the mutual information or information gain. Indeed, if one only considers the class label C and the current feature y, maximizing information gain corresponds to minimizing conditional entropy and this in turn minimizes a bound on classification error according to Fano's inequality.

With contextual information coming into play, mutual information between C and y alone cannot in general reveal the potential information gain; and one shall appeal only to the information gain criterion for the right answer. Since we have uncertainty in the contextual features, it is not a trivial task to formulate an information gain strategy directly. Based on different treatments of contextual uncertainties, the present invention incorporates three models: a mean imputation model, an integral model, and a sample-expectation model; or M-model, I-model, and S-model, respectively.

The M-model provides the most straightforward treatment. It assigns the mean values to the contextual features while working on the current feature. The information gain of y, $IG_y$, is defined as:

$$IG_y(C, X = \bar{x}, y \in \zeta) = \qquad (3)$$
$$H(C \mid X = \bar{x}, y \in \zeta) - \int_\zeta P(y \mid X = \bar{x}) H(C \mid X = \bar{x}, y) dy$$

where (4)
$$H(C \mid X = \bar{x}, y \in \zeta) =$$
$$-\sum_k P(C = c_k \mid X = \bar{x}, y \in \zeta) \log P(C = c_k \mid X = \bar{x}, y \in \zeta)$$

and (5)
$$P(C = c_k \mid X = \bar{x}, y \in \zeta) = \frac{P(C = c_k) \int_\zeta P(X = \bar{x}, y \mid C = c_k) dy}{\sum_k P(C = c_k) \int_\zeta P(X = \bar{x}, y \mid C = c_k) dy}$$

The M-model is the simplest and it is very efficient. It can be practically very useful in the following scenario: when all measurements are done (with a mean value and a small variance), the doctor wants to know which feature is more sensitive than others, i.e., whether perturbations (due to, say, human or machine error) in one feature will cause more fluctuation in the final diagnosis than those of other features. However, M-model did not utilize all the statistical information available.

The Integral Model (I-Model) considers the full range of the contextual features:

$$IG_y(C, X \in \chi, y \in \zeta) = \qquad (6)$$
$$H(C \mid X \in \chi, y \in \zeta) - \int_\zeta P(y \mid X \in \chi) H(C \mid X \in \chi, y) dy$$

where (7)
$$H(C \mid X \in \chi, y \in \zeta) =$$
$$-\sum_k P(C = c_k \mid X \in \chi, y \in \zeta) \log P(C = c_k \mid X \in \chi, y \in \zeta)$$

Here, $P(C \mid X \in \chi, y \in \zeta)$ is evaluated according to the likelihood sampling strategy discussed above. $H(C \mid X \in \chi, y)$ is defined in a similar fashion. The conditional probability can be expressed in terms of the likelihood as follows:

$$P(y \mid X \in \chi) = \frac{P(y, X \in \chi)}{P(X \in \chi)} \qquad (8)$$

$$= \frac{\sum_k P(C = c_k) P(y, X \in \chi \mid C = c_k)}{\int_\zeta \sum_k P(C = c_k) P(y, X \in \chi \mid C = c_k) dy}$$

$$= \frac{\sum_k P(C = c_k) \int_\chi P(y, X \mid C = c_k) dX}{\int_\zeta \sum_k P(C = c_k) \int_\chi P(y, X \mid C = c_k) dX dy}$$

$IG_y$ is now expressed in terms of $P(y, X \mid C)$, the prior distributions obtained through the generative classifier, and $P(C)$, the prior probability for each class. All the integrals can be estimated either analytically if closed-form models are available, or by sampling within the uncertain range. In terms of sampling, randomized sampling is preferred to a deterministic sampling for the serendipity that could be brought forth in the randomness; in other words, random sampling has the capability of capturing unexpected irregularity in distributions.

An example of an efficient sampling-based integral algorithm, CFS-I is shown below:

---

For every feature of interest y:
    $P_x = 0$; $Sum\_H_{yt} = 0$; $L_k = 0$, $k = 1, \ldots, K$;
    For every sample of y, $y_t$:
        $L_{yt,k} = 0$, $k = 1, \ldots, K$;
        For every sample of X, $X_j$:
            Accumulate $L_{yt,k}$ += $P(X_j, y_i \mid C = c_k)$;
        Calculate Bayesian posterior, $P_{yt,k}$, from $L_{yt,k}$;
        Calculate Entropy $H_{yt}$ over $P_{yt,k}$:

Calculate $P_{yt} = \sum_k L_{yt,k} P(C = c_k)$;

Accumulate $Sum\_H_{yt}$ += $P_{yt} H_{yt}$;
        Accumulate (marginalize): $P_x$ += $P_{yi}$;
        Accumulate $L_k$ += $L_{yt,k}$;
    Calculate Bayesian posterior, $P_k$, from $L_k$;
    Calculate Entropy $H_y$ over $P_k$;
    Calculate information gain: $IG_y = H_y - Sum\_H_{yt}/P_x$.

---

For the Sample-Expectation Model (S-model), the question to answer for the current feature is: "assuming that we knew the context, on average how much information could we gain from measuring the current feature?" The formula is:

$$EIG_{y|X}(C, X \in \chi, y \in \zeta) = E_X[IG_y(C, X, y \in \zeta)] \qquad (9)$$

$$= \int_\chi P(X \mid y \in \zeta) IG_y(C, X, y \in \zeta) dX$$

$$= \int_\chi P(X \mid y \in \zeta)(H(C \mid X, y \in \zeta) -$$

$$\int_\zeta P(y \mid X) H(C \mid X, y) dy) dX$$

An exemplary sampling-based implementation, CFS-S, is shown below:

---

For every feature of interest y:
    $P_y = 0$; $Accu\_IG_y = 0$;
    For every sample of X, $X_j$:
        $P_x = 0$; $Sum\_H_{yt} = 0$; $L_k = 0$, $k = 1, \ldots, K$;
        For every sample of y, $y_t$:
            Calculate $L_{yi,k} = P(X_j, y_i \mid C = c_k)$;
            Calculate Bayesian posterior, $P_{yt,k}$, from $L_{yt,k}$;
            Calculate Entropy $H_{yt}$ over $P_{yt,k}$;

Calculate $P_{yt} = \sum_k L_{yt,k} P(C = c_k)$;

Accumulate (i.e., marginalize): $P_x \mathrel{+}= P_{yt}$;
        Accumulate $Sum\_H_{yt} \mathrel{+}= P_{yt} H_{yt}$;
        Accumulate $L_k \mathrel{+}= L_{yt,k}$;

Calculate $P_{xj} = \sum_k L_k P(C = c_k)$;

Accumulate (i.e., marginalize): $P_y \mathrel{+}= P_{xj}$;
    Calculate Bayesian posterior, $P_k$, from $L_k$;
    Calculate Entropy $H_y$ over $P_k$;
    Accumulate the information gain:
    $WeightedSum\_IG_y \mathrel{+}= P_{xj}(H_y - Sum\_H_{yt}/P_x)$.
    $IG_y = WeightedSum\_IG_y / P_y$.

---

The sample-expectation model can also be defined more generally but in a similar fashion in the form of $EIG_{y|x}$, where x is only a subset of X.

The present invention devises a testing scheme that combines outputs from multiple models to expose complicated feature dependencies. By examining the outputs of both the I-model and the S-model different feature sensitivities or relevance scenarios are detected. The following table shows an example for two features, x and y:

TABLE 1

An example for joint analysis of two features

| $IG_x$ | $IG_y$ | $EIG_{x|y}$ | $EIG_{y|x}$ | $IG_{xy}$ | Relevant features | Notes |
|---|---|---|---|---|---|---|
| 0 | 0 | 0 | 0 | 0 | — | x, y: weak or no |
| 0 | 0 | + | + | + | x, y | Both strong, e.g., $C = x \oplus y$ |
| 0 | + | 0 | + | + | y | y: Strong; x: weak or no |
| + | 0 | + | 0 | + | x | x: Strong; y: weak or no |
| + | + | 0 | 0 | + | x, y | Both weak, e.g., $x = f(y)$ |
| + | + | + | + | + | x, y | Both strong |

It is worth noting that for the first five columns in Table 1, only three columns need to be calculated. Joint analysis of two features can only expose dependency involving less than three features. In case there are dependencies between more than two features, joint analysis of more than two features must be considered.

For example, if $C = x \oplus y \oplus z$, and we have another three redundant features, $x'=x$, $y'=y$, and $z'=z$, analyzing two features at a time and we will arrive at the first row of Table 1. Only joint three-feature analysis such as $IG_{x,y,z}$ can reveal the contributions of x or x', y or y', and z or z'.

An easy implementation for $IG_{x,y,z}$ or $EIG_{x,y,z|\_}$ is through nested calls to the single-feature IG function. For example, $$IG_{x,y,z} = IG_x + EIG_{y,z|x} = IG_x + \sum_i P(x_i) IG_{y,z|x=x_i} \quad (11)$$

$$= IG_x + \sum_i P(x_i)(IG_{y|x=x_i} + EIG_{z|x=x_i, y})$$

$$= IG_x + \sum_i P(x_i)\left(IG_{y|x=x_i} + \sum_j P(y_j) IG_{z|x=x_i, y=y_j}\right)$$

$$= IG_x + \sum_i P(x_i)\left(IG_{y|x=x_i} + \sum_j P(y_j) IG_{z|x=x_i, y=y_j}\right) \quad (12)$$

The present invention uses an induction algorithm that can learn probabilistic models from the training data. We use kernel discriminant analysis combined with generative modeling for this purpose. The kernel discriminant has been shown to have comparable performance as SVM. In addition, it can provide a low dimensional, non-linearly transformed subspace, in which simple probability models can be built. We use RBF kernel with an empirically determined spread.

It is often necessary to expect missing feature values in the training data during a medical diagnosis. Data imputation is applied through sampling to fill in missing or uncertain values for feature(s) y, based on p(y|x) where x represents the remaining features with known values. The term p(y|x) is estimated using the training set. Robust estimates are used to reduce the influence of outliers.

Having described embodiments for method for determining feature sensitivity during a medical examination, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A method for assigning patient-specific feature sensitivity values to a set of measurements to be taken during a medical procedure of a patient in order to provide a medical diagnosis, the method comprising;
    receiving data from a sensor representing a particular medical measurement for the patient;
    analyzing the particular medical measurement and context data with respect to one or more sets of training models;
    deriving patient-specific feature sensitivity values for the particular medical measurement and other currently unknown measurements which may be taken for the patient based on the analysis;
    outputting the patient-specific feature sensitivity values for the particular measurement and the other currently unknown measurements based upon the derived feature sensitivity values for said particular medical measurement; and
    recommending additional measurements for one or more of the currently unknown measurements to be taken for the patient that have high feature sensitivity values based upon said outputted feature sensitivity values.

2. The method of claim 1 wherein the medical procedure is an echocardiogram examination.

3. The method of claim 1 wherein the context data comprises vital statistics relating to the patient.

4. The method of claim 3 wherein the vital statistics include the patient's age.

5. The method of claim 3 wherein the vital statistics include the patient's height.

6. The method of claim 3 wherein the vital statistics include the patient's weight.

7. The method of claim 3 wherein the vital statistics include the patient's blood pressure measurements.

8. The method of claim 1 wherein the context data comprises the patient's symptoms.

9. The method of claim 8 wherein the symptoms include indications of pain.

10. The method of claim 8 wherein the symptoms include shortness of breadth.

11. The method of claim 1 wherein context data comprises baseline test data for the patient.

12. The method of claim 1 wherein the medical sensor is an ultrasound transducer.

13. The method of claim 12 wherein the received data is image data.

14. The method of claim 1 wherein the analyzing step further comprises the step of:
analyzing the received data, context data and training models using an integral model.

15. The method of claim 1 wherein the analyzing step further comprises the step of:
analyzing the received data, context data and training models using a sample expectation model.

16. The method of claim 1 wherein the analyzing step further comprises the step of:
analyzing the received data, context data and training models using both an integral model and a sampling expectation model.

17. The method of claim 1 wherein the step of outputting the patient-specific feature sensitivity values further comprises the step of:
providing an indication of a probability for one or more medical diagnosis; and
providing a listing of potential measurements for the patient wherein a feature sensitivity value is assigned to each currently unknown measurement.

18. The method of claim 17 further comprising the steps of:
receiving input representing a selection of one or more currently unknown measurements for the patient for which measurements are to be taken;
receiving data from the medical sensor corresponding to the selected one or more currently unknown measurements for the patient;
analyzing the received data for the selected one or more currently unknown measurements, data corresponding to any prior measurements and context data with the training models;
deriving patient specific feature sensitivity values for the set of currently unknown measurements; and
outputting the patient specific feature sensitivity values.

19. The method of claim 1 wherein a user uses the outputted feature sensitivity values to assist in making a medical diagnosis.

20. The method of claim 1 wherein the outputted feature sensitivity values are provided in real time.

21. A system for assigning patient-specific feature sensitivity values to a set of currently unknown measurements to be taken during a medical procedure of a patient in order to provide a medical diagnosis, the system comprising:
a medical sensor that provides medical measurements taken of a patient;
a processor connected to the medical sensor, the processor receiving the medical measurements for the patient taken by the medical sensor and context data relating to the patient, the processor analyzing the sensor measurements and context data and determining patient specific feature sensitivity values for the set of currently unknown measurements which may be taken by the sensor based upon the determined feature sensitivity values of the analyzed sensor measurements and context data, the processor further recommending which additional measurements of the currently unknown measurements should be taken for the patient based on the patient specific feature sensitivity values; and
a display device for displaying the sensor data and determined feature sensitivity values.

22. The system of claim 21 further comprising a database associated with the processor, the database including a set of training models that are compared to the context data and sensor measurements for the patient in order to obtain patient specific feature sensitivity values for the set of currently unknown measurements.

23. The system of claim 21 wherein the medical sensor is an ultrasound transducer.

24. The system of claim 21 wherein the medical procedure is an echocardiogram examination.

25. The system of claim 21 wherein the context data comprises vital statistics relating to the patient.

26. The system of claim 25 wherein the vital statistics include the patient's age.

27. The system of claim 25 wherein the vital statistics include the patient's height.

28. The system of claim 25 wherein the vital statistics include the patient's weight.

29. The system of claim 25 wherein the vital statistics include the patient's blood pressure measurements.

30. The system of claim 21 wherein the context data comprises the patient's symptoms.

31. The system of claim 30 wherein the symptoms include indications of pain.

32. The system of claim 30 wherein the symptoms include shortness of breadth.

33. The system of claim 21 wherein context data comprises baseline test data for the patient.

34. The system of claim 21 wherein a user uses the determined feature sensitivity values to assist in making a medical diagnosis.

35. The system of claim 21 wherein the determined feature sensitivity values are provided in real time.

36. The system of claim 21 wherein context data comprises medical measurements from a patient's prior medical examinations.

* * * * *